(12) United States Patent
Obaidat et al.

(10) Patent No.: US 9,862,780 B1
(45) Date of Patent: Jan. 9, 2018

(54) PROCESS OF PRODUCING AND METHOD OF USING SOLUBLE HIGH MOLECULAR-WEIGHT CHITOSAN

(71) Applicant: Jordan University of Science and Technology, Irbid (JO)

(72) Inventors: Rana M. Obaidat, Irbid (JO); Adnan Badwan, Naor (JO)

(73) Assignee: Jordan University of Science and Technology, Irbid (JO)

( * ) Notice: Subject to any disclaimer, the term of this patent is extended or adjusted under 35 U.S.C. 154(b) by 0 days.

(21) Appl. No.: 15/413,942

(22) Filed: Jan. 24, 2017

(51) Int. Cl.
| | |
|---|---|
| C08B 37/08 | (2006.01) |
| A01N 25/08 | (2006.01) |
| A01N 43/16 | (2006.01) |
| A61L 15/44 | (2006.01) |
| A61L 15/28 | (2006.01) |
| A23P 20/10 | (2016.01) |
| A23L 33/10 | (2016.01) |

(52) U.S. Cl.
CPC ............ *C08B 37/003* (2013.01); *A01N 25/08* (2013.01); *A01N 43/16* (2013.01); *A23L 33/10* (2016.08); *A23P 20/10* (2016.08); *A61L 15/28* (2013.01); *A61L 15/44* (2013.01); *A23V 2002/00* (2013.01); *A61L 2300/232* (2013.01); *A61L 2300/406* (2013.01); *A61L 2420/02* (2013.01)

(58) Field of Classification Search
None
See application file for complete search history.

(56) References Cited

U.S. PATENT DOCUMENTS

2003/0133891 A1 * 7/2003 Panzer ................ A61K 8/0241
424/65

* cited by examiner

*Primary Examiner* — Brian Gulledge
(74) *Attorney, Agent, or Firm* — SV Patent Service

(57) ABSTRACT

A process for preparing a soluble high molecular-weight chitosan which comprises treating chitosan, water, alcohol, acid mixture with supercritical fluid to prepare a modified chitosan with high aqueous solubility.

20 Claims, 16 Drawing Sheets

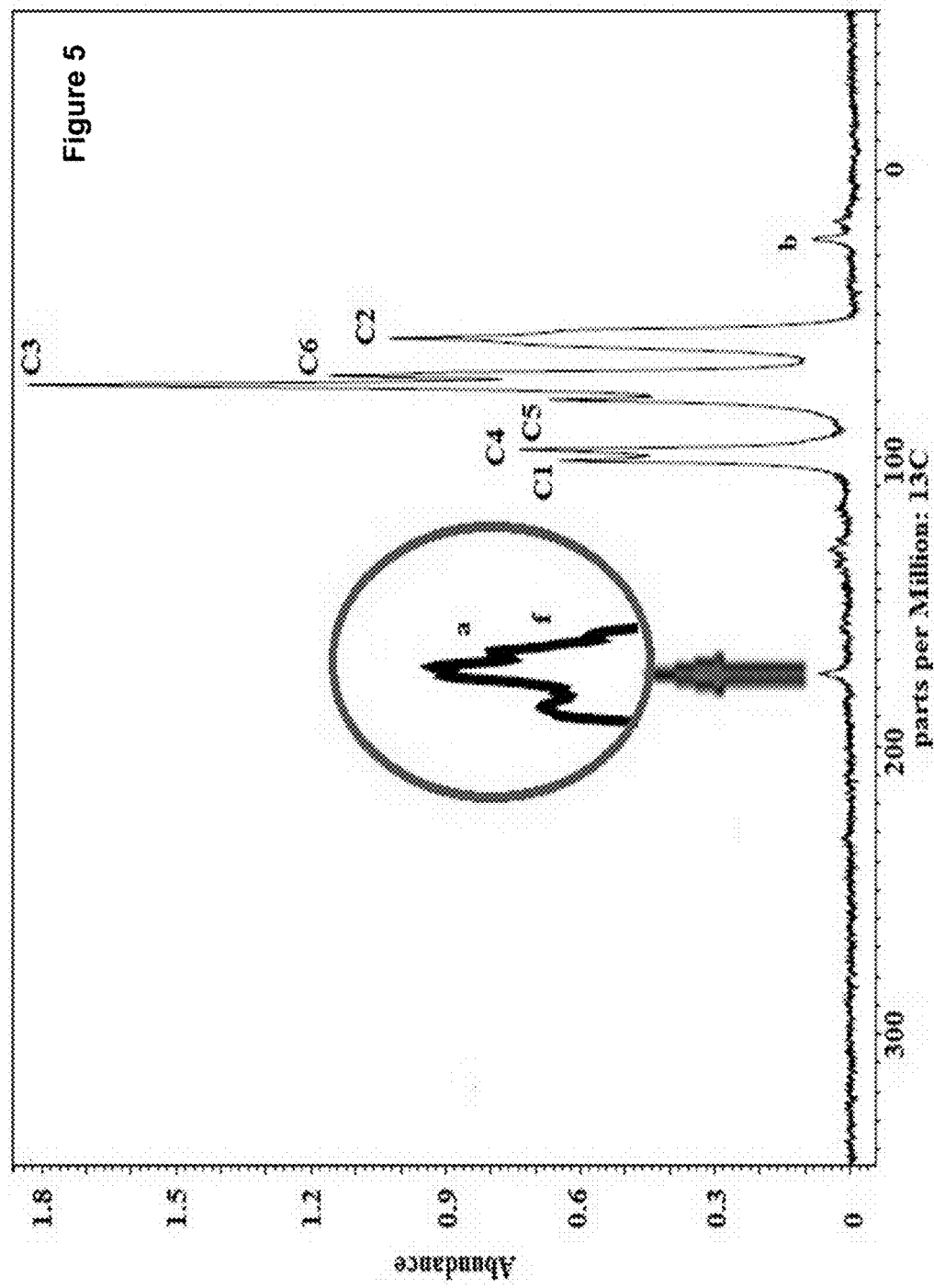

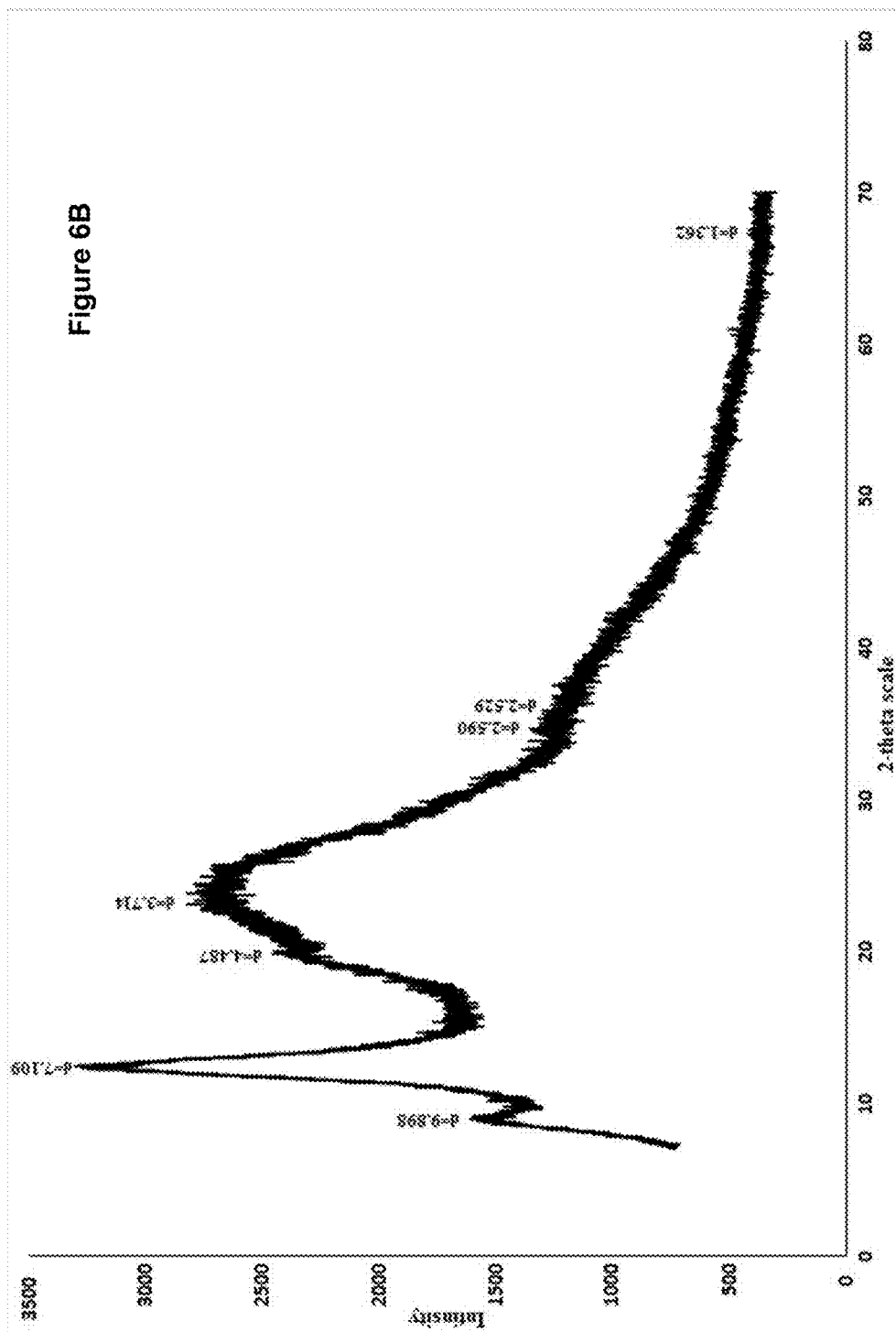

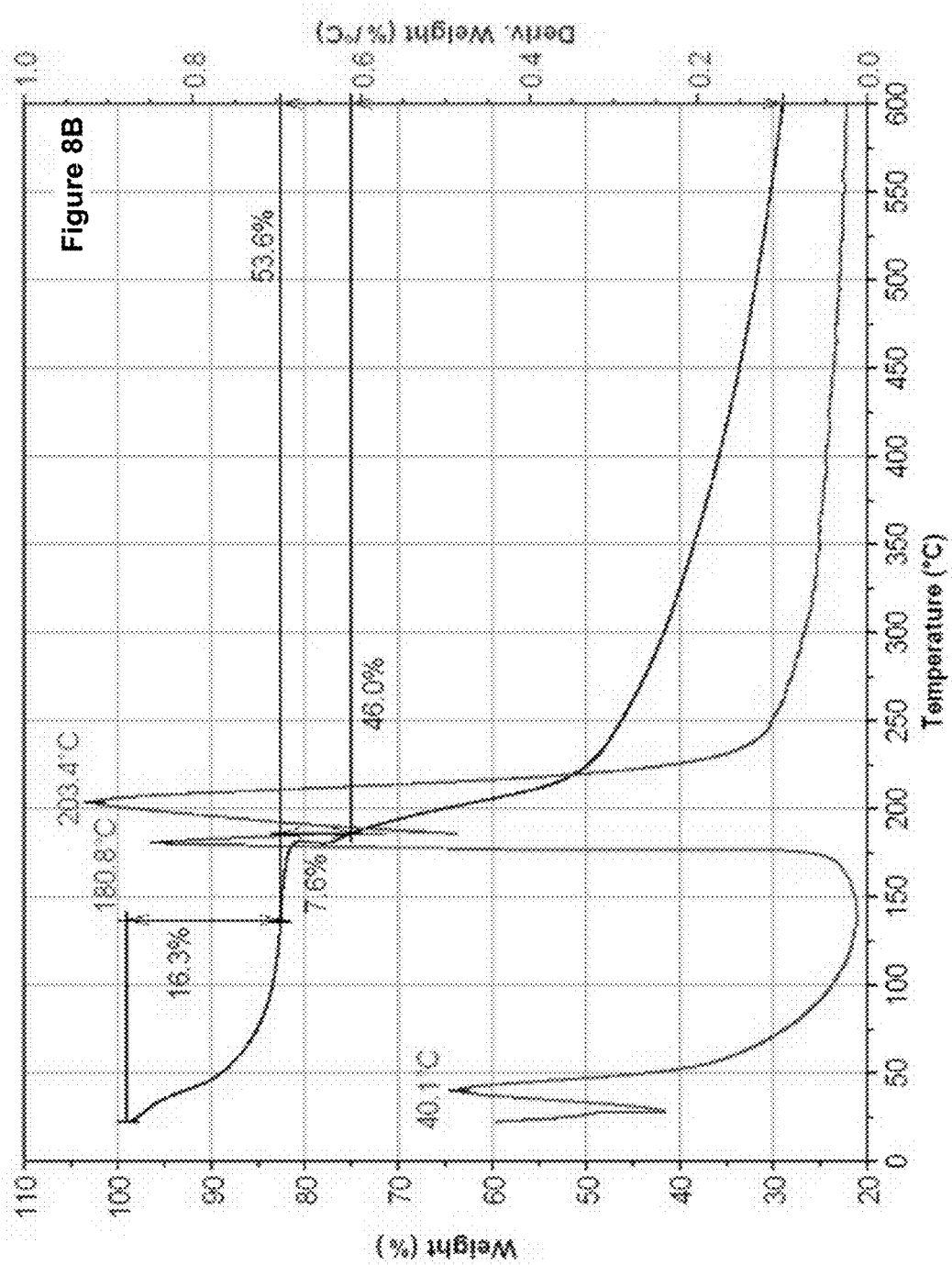

PROCESS OF PRODUCING AND METHOD OF USING SOLUBLE HIGH MOLECULAR-WEIGHT CHITOSAN

BACKGROUND OF THE INVENTION

The present invention is related to the technical field of preparing and using soluble high molecular-weight chitosan.

Low water solubility has restricted applications of chitin (FIG. 1A), which resulted in the expanded use of its water-soluble derivatives chitosan (FIG. 1B). Chitosan, which is produced by deacetylation of chitin, offers many biomedical advantages, and has wide applications in the pharmaceutical and biomedical areas. The solubility of chitosan in water is limited to pH values lower than 6, wherein the glucosamine moiety is converted to $R-NH_3^+$ soluble form by the protonation of amine group. Although it was soluble at pH below 6, chitosan dispersions suffer from aggregation. The formation of these aggregates is related to interactions between the hydrophobic parts in different chitosan molecules as well as hydrogen bonding between chitosan molecules. The aggregation of chitosan molecules decreases their interactions with water.

Several studies were conducted in attempt to enhance solubility of chitosan in water. The main methods have focused on preparation of small molecular-weight oligomers, changing the degree of deacetylation, and chemical modification such as the preparation of carboxymethyl chitosan.

U.S. Pat. No. 6,716,970 has disclosed a method of acetylation of chitosan to produce water-soluble derivative at pH values between 6 and 8. Patent CN 102786607 teaches a method of producing water-soluble chitosan oligosaccharides by hydrolysis using hydrogen peroxide at increase temperatures. Patent CN 02321194 describes facilitation of chitosan hydrolysis when subjected to ultrasonication. Patent WO2014014370A2 has disclosed a method for obtaining aqueous solution of chitosan. Another patent CN 103113490A has described preparation of water-soluble chitosan phosphate derivatives to be used as metal corrosion inhibitor. Korean patent 441270 has described the preparation of water-soluble free amine chitosan (1000-100.000 Da) by treatment of acidic solution of chitosan with trialkylamine with addition of organic solvent to remove the organic acid, followed by a purification step using activated carbon/ion exchange column. The prepared polymer is claimed to be non-toxic and biocompatible. US Patent Publication 20100040694 relates to preparation of low-molecular weight water-soluble chitosan nanoparticles for gene delivery with folic acid conjugates. Another patent WO2007013717 has disclosed preparation of high quality water-soluble chitosan oligosaccharide (1000-11.000 Da) using ultrafiltration by freeze drying, introduction of organic solvent, and vacuum drying.

However, the above described methods suffer from several disadvantages, which include reproducibility issues even for skilled people, difficulties in scaling up for industrial applications, significant time consumption, the requirement of large amounts of solvents, and finally changes in the important characteristics of the prepared polymers such as reduction of the molecular weight of the polymers. The disclosed methods also change other important physicochemical properties such as viscosity, degree of deacetylation, particle size, and density, which affect many practical applications in the pharmaceutical field and the food industry. Chemical derivatization in many studies has the drawback in complex multi-stage procedures and the use of organic solvents which are harmful for the health and environment. In addition, the chitosan derivatives do not maintain biocompatibility and stability compared to non-modified chitosan.

Supercritical fluid technique offers many advantages over other techniques. It decreases consumption of organic solvents and is thus a greener technology. The procedure can be carried at moderate temperatures, with the capability to control particle size and morphology. This technology has wide applications, including extraction, particle generation, preparation of inclusion complexes, and chemical reactions that require high speed. $CO_2$ is the most commonly used substance in supercritical fluid technology. It offers many advantages over other substances. It can be used at moderate processing parameters, with a critical temperature of 31.1° C. and a critical pressure of 73.8 bar. It is inflammable, not toxic, and available at low cost. Patent PL 198876 teaches a method of obtaining dry chitosan membrane using supercritical fluid technology.

The presence of primary amino and two hydroxyl groups in chitosan allows the possibility of chemical modification in the structure. Although chitosan is insoluble in supercritical fluid $CO_2$, solubility of $CO_2$ is expected to be high in chitosan. This property leads to swelling of the polymeric chains, causing plasticization, which in turn can increase segmental and chain mobility, causing an increase in the inter chain distance. The main advantage in this state is that molecular weight of the polymer is of little influence on the swelling. Another advantage is in the enhancement of $CO_2$ diffusion inside the polymeric chain, which facilitates interaction between $CO_2$ and the polymer.

However, there have been limited studies concerning polymeric modification of chitosan using supercritical fluid $CO_2$. There is still a need for a method to increase chitosan's water solubility at median pH values.

SUMMARY OF THE INVENTION

The present invention discloses a method for preparing high molecular-weight chitosan soluble in water.

In one general aspect, the present invention relates to a method for the preparation of high molecular-weight chitosan. The method includes introducing a mixture of input chitosan, alkyl alcohol, water, and an acid into a supercritical fluid vessel, heating the mixture in the supercritical fluid vessel to an elevated temperature, incubating the mixture at a supercritical pressure for a period of incubation time in the supercritical fluid vessel, depressurizing the mixture in the supercritical fluid vessel, cooling the mixture in the supercritical fluid vessel to room temperature, and collecting a powder comprising water-soluble high molecular-weight chitosan from the supercritical fluid vessel.

Implementations of the system may include one or more of the following. The input chitosan can have a molecular weight in the range 100 kDa to 600 kDa. The input chitosan can have a degree of aceylation higher than 50%. The alkyl alcohol can have a carbon number in a range $C_3$ to $C_4$ in the chain hydrocarbon chain. The alkyl alcohol can include ethanol. The mixture can include from 5% to 95% of alkyl alcohol based on volume. The acid can include an organic acid or an inorganic acid. The inorganic acid can include hydrochloric acid. The mixture can include from 10% to 50% of the hydrochloric acid based on the volume of the mixture. The mixture can include from 10% to 90% of water based on volume. The elevated temperature in the step of heating can be in the range 40° C. to 100° C. The pressure in the step of incubating can be in the range 40 bar to 100 bar. The step of incubating can have an incubation time in is in the range 1 to 3 hours. The mixture can include NaCl, CaCl$_2$, or an organic co-solvent. The water-soluble high molecular-weight chitosan can have an average molecular weight in the range from 500 kDa to 10000 kDa, wherein the water-soluble high molecular-weight chitosan has a viscosity from 500 cps to 5000 cps. The water-soluble high molecular-weight chitosan can have water solubility more than 1% in weight/volume concentration. The method can further include dissolving the water-soluble high molecular-weight chitosan in water to form a polymer solution; and forming a film using the polymer solution comprising the water-soluble high molecular-weight chitosan. The method can further include dissolving the water-soluble high molecular-weight chitosan in water to form a polymer solution; and coating a food item using the polymer solution. The method can further include dissolving the water-soluble high molecular-weight chitosan in water to form a polymer solution; and coating a substrate item using the polymer solution to provide anti-bacterial function. The step of coating can include atomizing the polymer solution to form an atomized polymer solution; and spraying the atomized polymer solution on the food item.

Embodiments may include one or more of the following advantages. The disclosed method provides for fast, single-step, and low cost of production of water-soluble high molecular-weight chitosan. The prepared polymers show autonomous gelling property: gelling can occur by simply mixing the prepared polymers with water, and viscosity can be controlled by changing the concentration of added amount.

Although the invention has been particularly shown and described with reference to multiple embodiments, it will be understood by persons skilled in the relevant art that various changes in form and details can be made therein without departing from the spirit and scope of the invention.

BRIEF DESCRIPTION OF THE DRAWINGS

The following drawings, which are incorporated in and form a part of the specification, illustrate embodiments of the present invention and, together with the description, serve to explain the principles of the invention.

FIG. 5 shows an exemplified solid state 13C-NMR spectrum of the modified water-soluble high molecular-weight chitosan in accordance with the present invention.

FIGS. 6A and 6B show powder X-ray diffraction intensity distributions respectively for input chitosan (6A) and water-soluble high molecular-weight chitosan (6B).

FIGS. 8A and 8B show exemplified thermal analysis thermograms respectively for input chitosan (8A) and water-soluble high molecular-weight chitosan (8B).

DETAILED DESCRIPTION OF THE INVENTION

Figure 1:
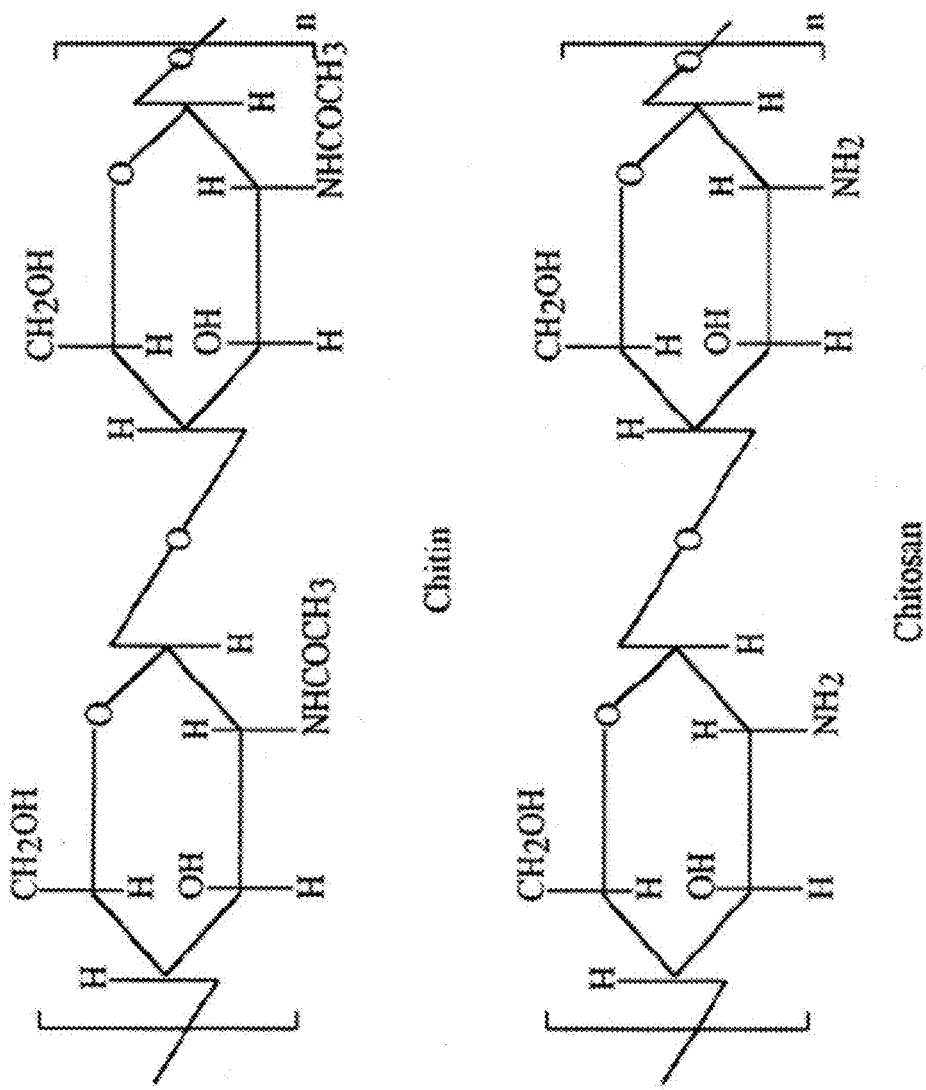
FIGS. 1A and 1B respectively show structures of chitin and chitosan.
Figure 2:
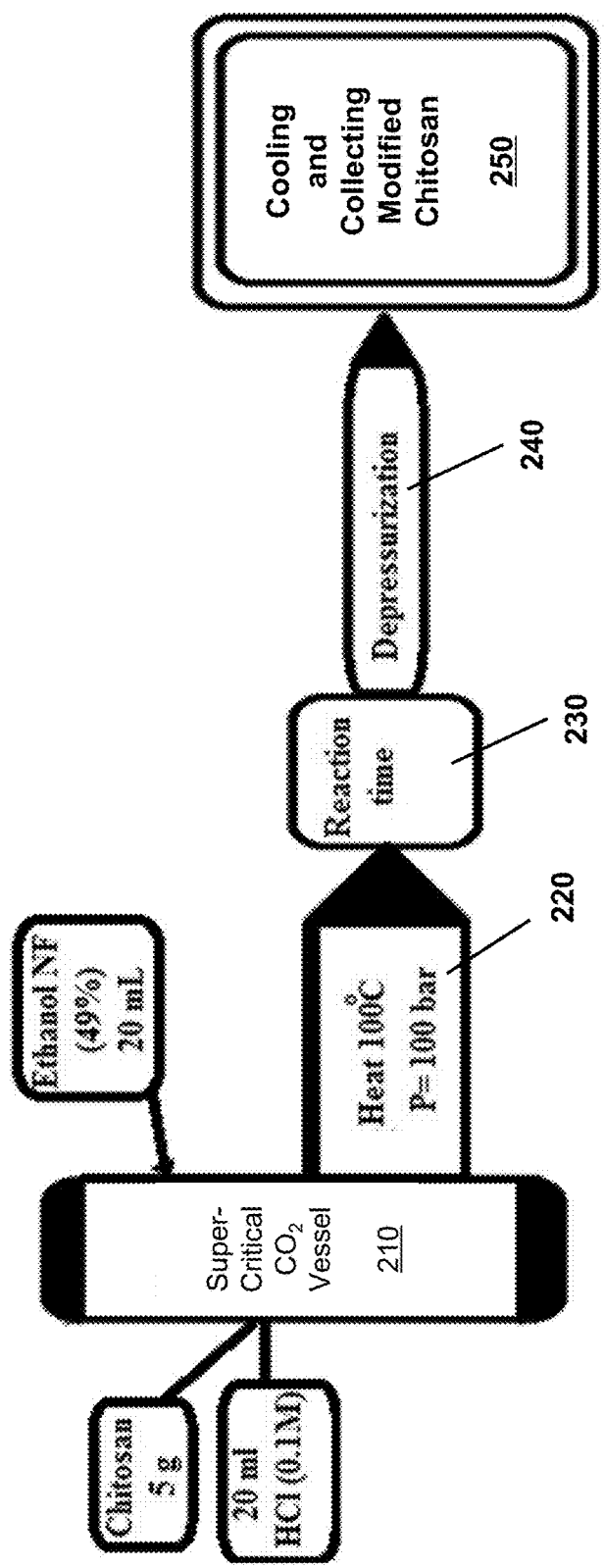
FIG. 2 is a schematic diagram of the workflow for producing water-soluble high molecular-weight chitosan modified chitosan using supercritical fluid CO$_2$ in accordance with the present invention.

The present invention relates to the use of the supercritical fluid method to produce water-soluble high molecular-weight chitosan. The presently disclosed method modifies chitosan using supercritical fluid CO$_2$ to enhance its water solubility in the pH range between 6 and 8. Referring to FIG. 2, the preparation method includes one or more of the following steps: First, a chitosan powder, an alkyl alcohol such as ethanol, an acid such as an organic acid or inorganic acid (e.g. hydrochloric acid), and water are introduced into a supercritical fluid vessel (step 210). The chitosan powder contains input chitosan. Next, the solution (or the mixture) in the supercritical fluid vessel is heated up to a high temperature (step 220). The mixture is subsequently incubated at a supercritical pressure for time less than 3 hours (step 230). The solution is depressurized (step 240). The solution is then cooled to room temperature and the resulting dried powder is collected (step 250). The resulting dried powder contains water-soluble polymeric or high molecular-weight chitosan. In some embodiments, gases other than CO$_2$ can be employed in the supercritical fluid.

The disclosed preparation method of the water-soluble high molecular-weight chitosan can use input chitosan having a molecular weight in the range 100 kDa to 600 kDa, or preferably in the range 50 to 100 kD, or in the range 20 KDa to 50 kDa. The input chitosan has a degree of aceylation higher than 50%, preferably higher than 70%, or higher than 85%. The alkyl alcohol has a carbon number in a range C$_3$ to C$_4$ in the chain hydrocarbon chain, more preferably in the range C$_2$ to C$_3$. The input Chitosan can be placed in the supercritical fluid vessel with addition of a ternary solvent system composed of ethanol, HCl, and H$_2$O in a 2:1:1.5 ratio. In some embodiments, salts such as NaCl, CaCl$_2$ and/or other organic co-solvents can be used. A critical variable in the experiments conducted was the ratio and the total mixture volume of the solvents (ethanol, HCl, H2O) to the volume of supercritical fluid extraction vessel (supercritical CO$_2$). In our experiments, this ratio did not exceed 60%.

The mixture in the supercritical fluid vessel can include from 10% to 50% of hydrochloric acid based on the volume of the mixture. The mixture in the supercritical fluid vessel can include from 5% to 95% of alkyl alcohol based on volume, or preferably 60% to 80%, or 50% to 70%, or 20%-50%, or 15-30% of alkyl alcohol based on volume. The mixture in the supercritical fluid vessel can include 10%-90% of water based on volume, or preferably 20%-70%, or 20%-40% of water based on volume of the mixture.

The temperature in the supercritical fluid vessel in step 230 can be in the range from 40° C. to 100° C., or preferably from 60° C. to 100° C., or from 90° C. to 100° C. The pressure in the supercritical fluid vessel in step 230 can be in the range 40 bar to 100 bar, preferably in the range 60 bar to 100 bar and more preferably in the range 90 to 100 bar. The incubation time in the supercritical fluid vessel in step 230 can be in the range 1 to 3 hours. The prepared water-soluble high molecular-weight chitosan can have an average molecular weight in the range from 500 kDa to 10000 kDa, or preferably in the range 1000 KDa to 6000 kDa, or in the range 1000 KDa to 4000 kDa.

The molecular weight of the prepared water-soluble high molecular-weight chitosan can be higher than 2 times of the molecular weight of the input chitosan. The viscosity of 10% prepared water-soluble polymeric solution can have viscosity from 500 cps to 5000 cps, or preferably in the range 1000 cps to 5000 cps, or in the range 2000 cps to 5000 cps. The prepared water-soluble high molecular-weight chitosan can have water solubility more than 1% in weight/volume concentration, or preferably more than 2%, or more than 4%.

Example 1

Figure 3A:
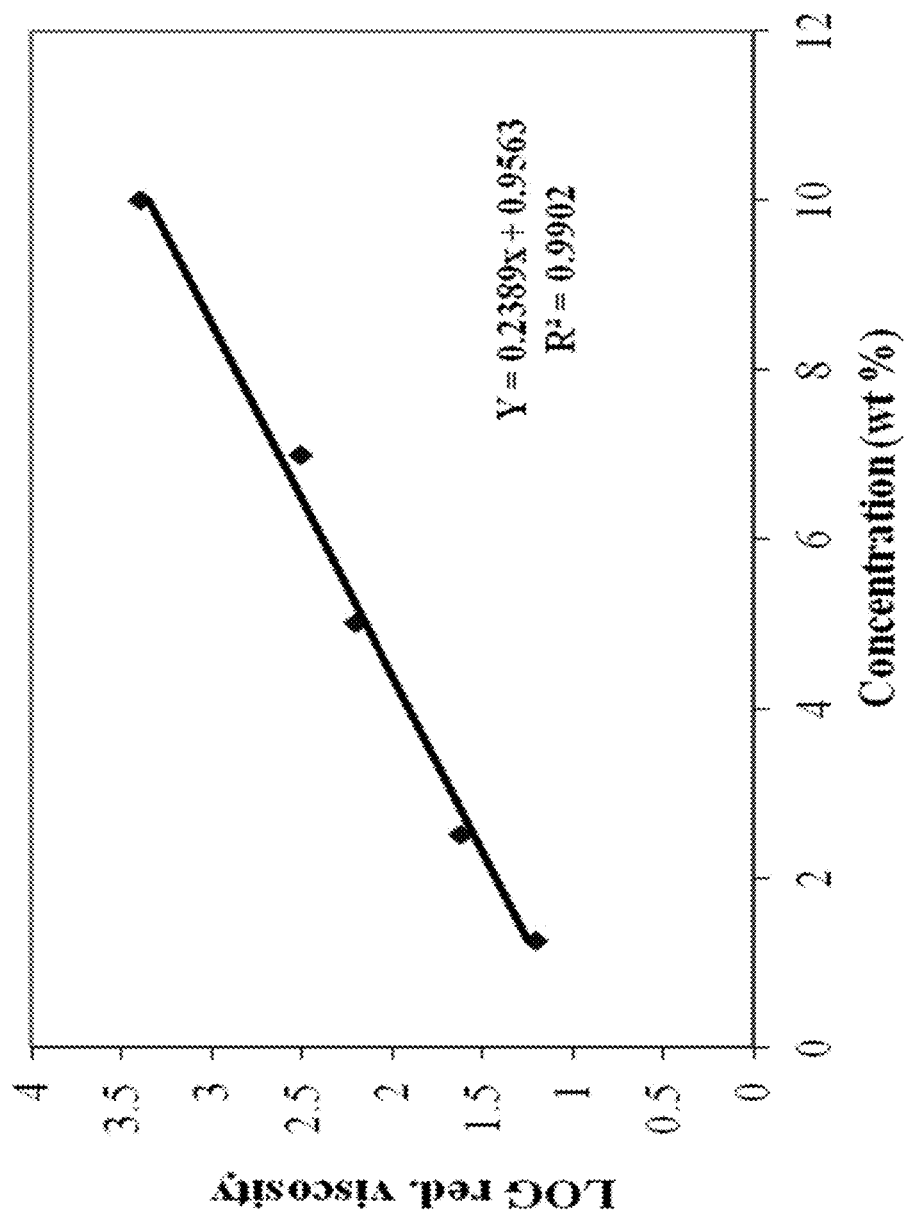
FIGS. 3A-3D show exemplified data plots for determining molecular weights of water-soluble high molecular-weight chitosan using Mark-Houwink equation in accordance with the present invention.

Preparation of High Molecular-Weight Chitosan of Average Molecular Weight $1.11 \times 10^6$ Dalton Five grams chitosan was mixed with 20 mL ethanol, 15 mL distilled water, and 10 mL hydrochloric acid inside the supercritical fluid vessel. The supercritical fluid vessel was heated up to 100° C. at a pressure of 100 bar for 1 hour. Then solution is then depressurized and cooled to room temperature. The water-soluble chitosan obtained has high molecular-weight of an average value equal to $1.11 \times 10^6$ Dalton as determined by application of Mark-Houwink equation (FIG. 3A).

Example 2

Figure 3B:
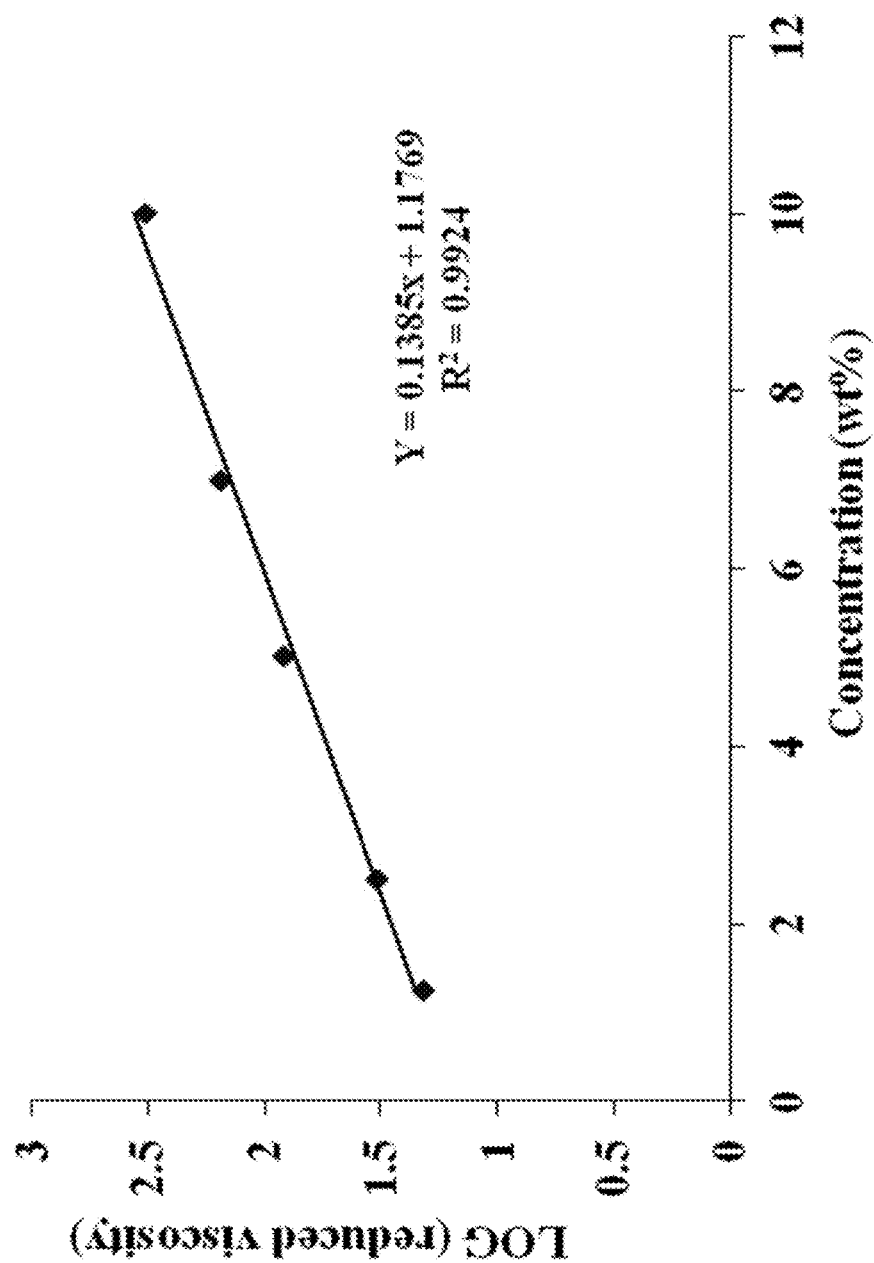

Preparation of High Molecular-Weight Chitosan of Average Molecular Weight $2.31 \times 10^6$ Dalton Five grams chitosan was mixed with 20 mL ethanol, 15 mL distilled water, and 10 mL hydrochloric acid inside the supercritical fluid vessel. The supercritical fluid vessel was heated up to 100° C. at a pressure of 100 bar for 2 hours. Then solution is then depressurized and cooled to room temperature. The water-soluble chitosan obtained has high molecular-weight of an average value equal to $2.31 \times 10^6$ Dalton as determined by application of Mark-Houwink equation (FIG. 3B).

Example 3

Figure 3C:
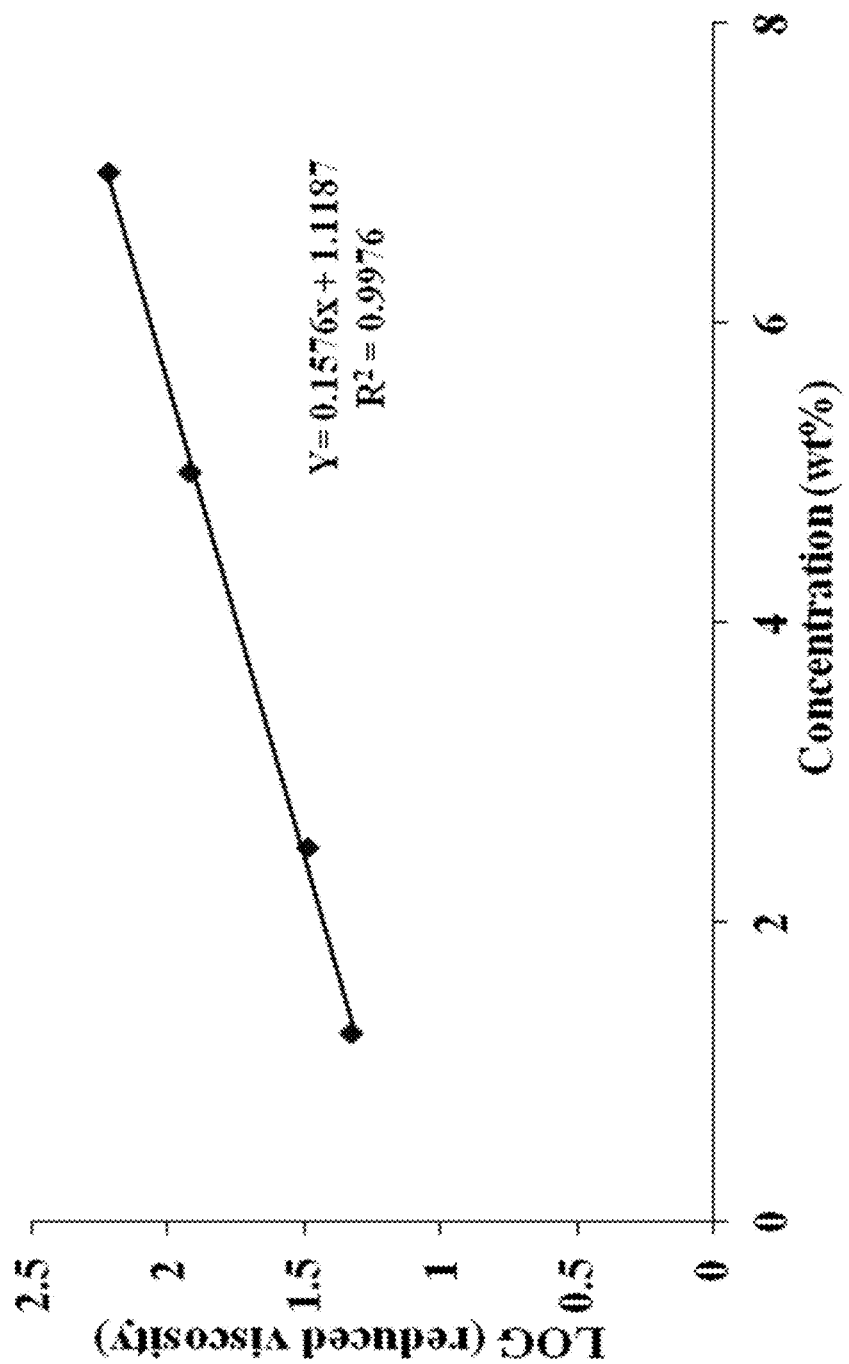

Preparation of High Molecular-Weight Chitosan of Average Molecular Weight $1.9 \times 10^6$ Dalton Five grams chitosan was mixed with 20 mL ethanol, 15 mL distilled water, 10 mL hydrochloric acid, and additional 0.5 g NaCl inside the supercritical fluid vessel. The supercritical fluid vessel was heated up to 100° C. at a pressure of 100 bar for 2 hours. Then solution is then depressurized and cooled to room temperature. The resulting dried powder is collected. The water-soluble chitosan obtained has high molecular-weight of an average value equal to $1.9 \times 10^6$ Dalton as determined by application of Mark-Houwink equation (FIG. 3C).

Example 4

Figure 3D:
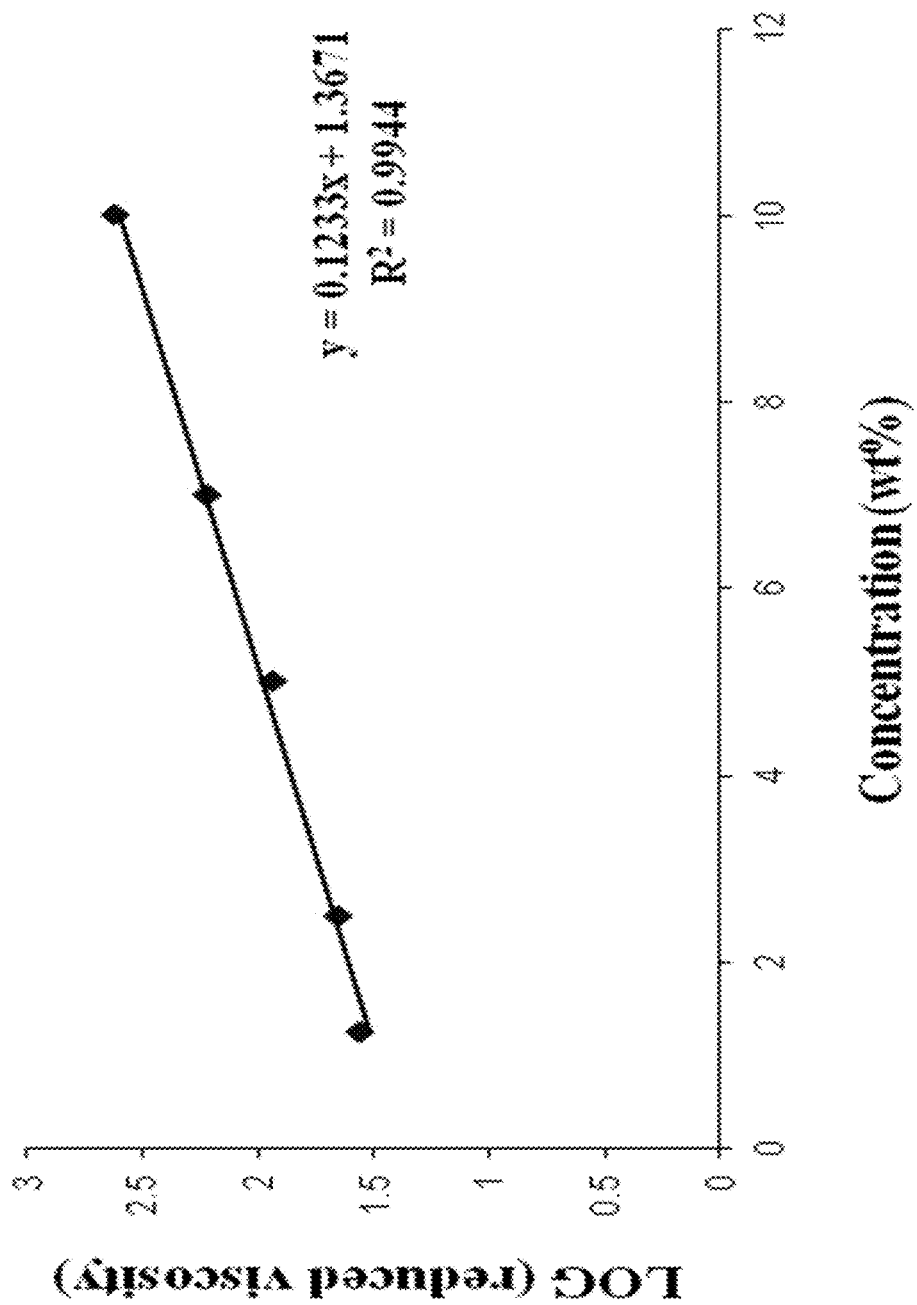
Figure 4:
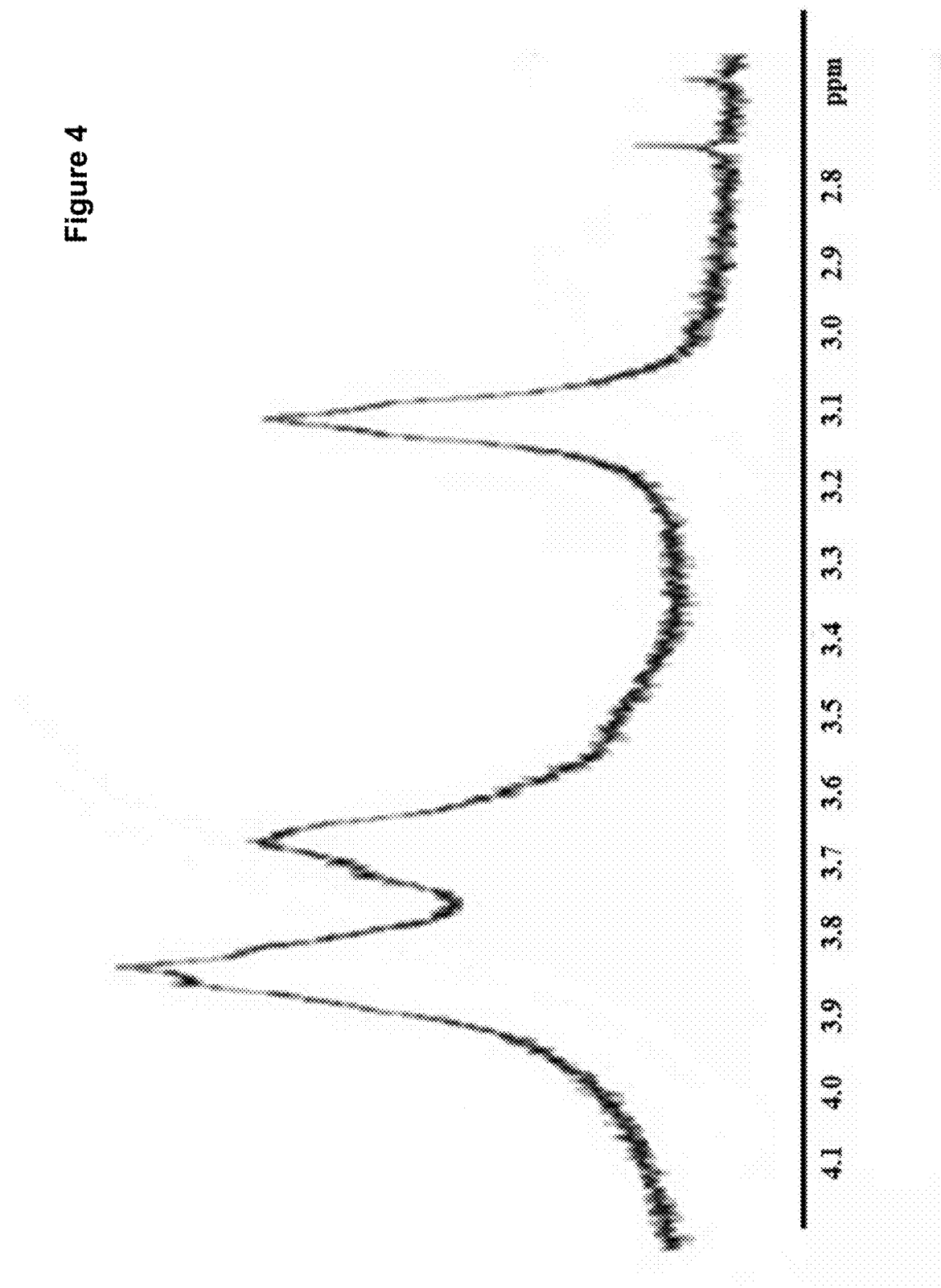
FIG. 4 shows an exemplified 1H-NMR spectrum for the modified water-soluble high molecular-weight chitosan in accordance with the present invention.

Preparation of High Molecular-Weight Chitosan of Average Molecular Weight $4.35 \times 10^6$ Dalton Ten grams chitosan was mixed with 40 mL ethanol, 30 mL distilled water, and 20 mL hydrochloric acid inside the supercritical fluid vessel. The supercritical fluid vessel was heated up to 100° C. at a pressure of 100 bar for 1 hour. Then solution is then depressurized and cooled to room temperature. The water-soluble chitosan obtained has high molecular-weight of an average value equal to $4.35 \times 10^6$ Dalton as determined by application of Mark-Houwink equation (FIG. 3D).

Example 5

Film Forming

A polymeric solution was prepared by dissolving 2 g of water-soluble high molecular-weight chitosan, produced by one of the above methods, in 100 ml of water. After 20 minutes of centrifugation, which removes air pulps from the polymeric solution, a measured volume of each polymeric solution (20 ml) was poured into petri-dish, which was then kept at room temperature for 48 h. The dried films were peeled from the Petri dishes.

Example 6

Tablet Film Coating
Compositions of Coating Mixture Prepared Based on the Water-Soluble High Molecular-Weight Chitosan (Modified Chitosan)

| Component | Percentage (weight per weight) |
|---|---|
| Modified chirtosan | 55%-75% |
| Titanim dioxide | 20%-30% |
| Polyethylene glycol | 5%-10% |
| Triacetin | 1%-2% |
| Coloring agent | 0.5%-1.0% |

A suspension of the coating mixture was prepared by adding the coating mixture (15% to 25% weight per weight) to the volume of water (65 to 85% weight per weight) gradually and mixing for 45 minutes. The spraying suspension was filled into an atomizer. The uncoated tablets were introduced to the coating machine pan and warmed using hot air. The coating machine parameters were adjusted; the tablets were sprayed to obtain a constant average weight (the coating mixture represents a range from 2% to 5% to the total weight of the tablet). White beeswax can be used to polish the tablets.

Example 7

Anti-Bacterial Effect

One and half gram of the water-soluble high molecular-weight chitosan was dissolved in 5 mL of water. The resulting polymer solution is coated on a substrate such as textile, a fabric, and a medical bandage. Antibacterial effect was tested against 2 bacterial strains (*E. Coli* 25922 as gram negative bacteria and *Staph. Aureus* 29213 as gram positive bacteria). Disk diffusion technique was employed with impregnation of known amount from test samples. Negative controls were used with sterile disc impregnated with water only. The impregnated discs were kept at the center of agar plates, seeded with test bacterial cultures. The discs were then placed individually using a sterile forceps in appropriate grids which were marked on the undersurface of the plated Petri plates and kept for incubation at room temperature (27° C.±2) for 24 h. After incubation, plates were observed and showed clear zones of inhibition for the bacterial strains.

Figure 6A:
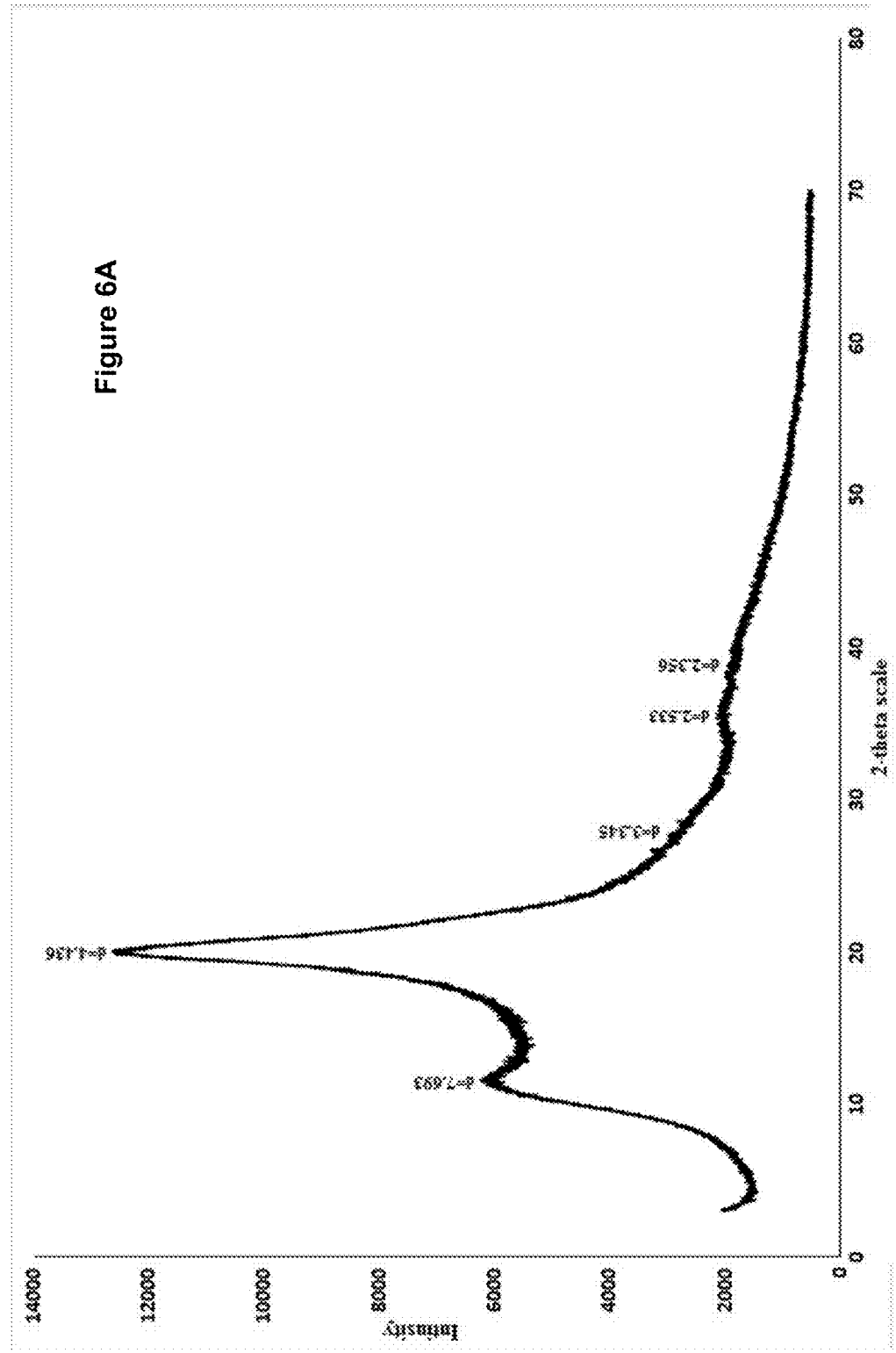
Figure 7A:
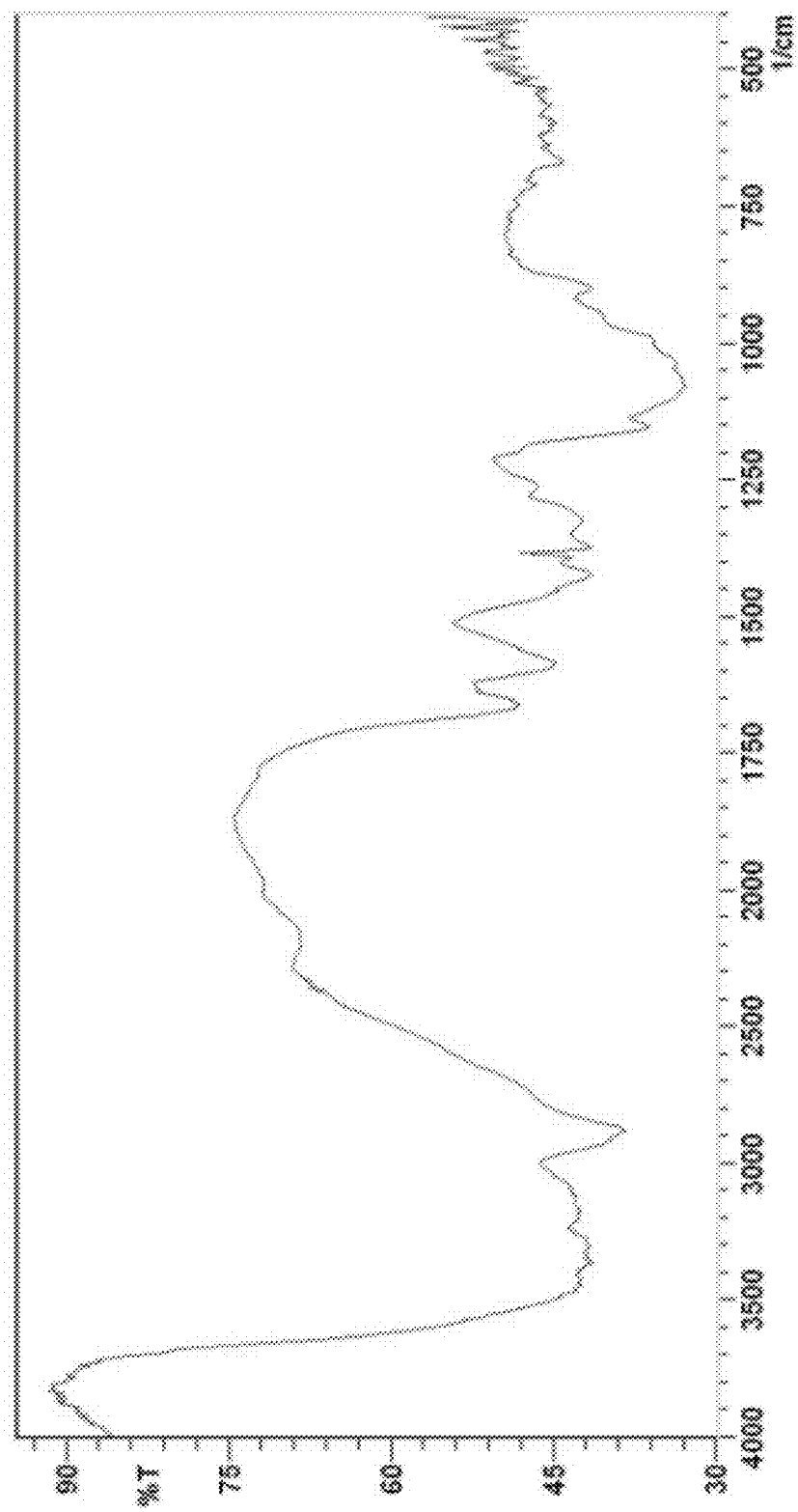
FIGS. 7A and 7B show exemplified FTIR spectra respectively for input chitosan (7A) and water-soluble high molecular-weight chitosan (7B).
Figure 7B:
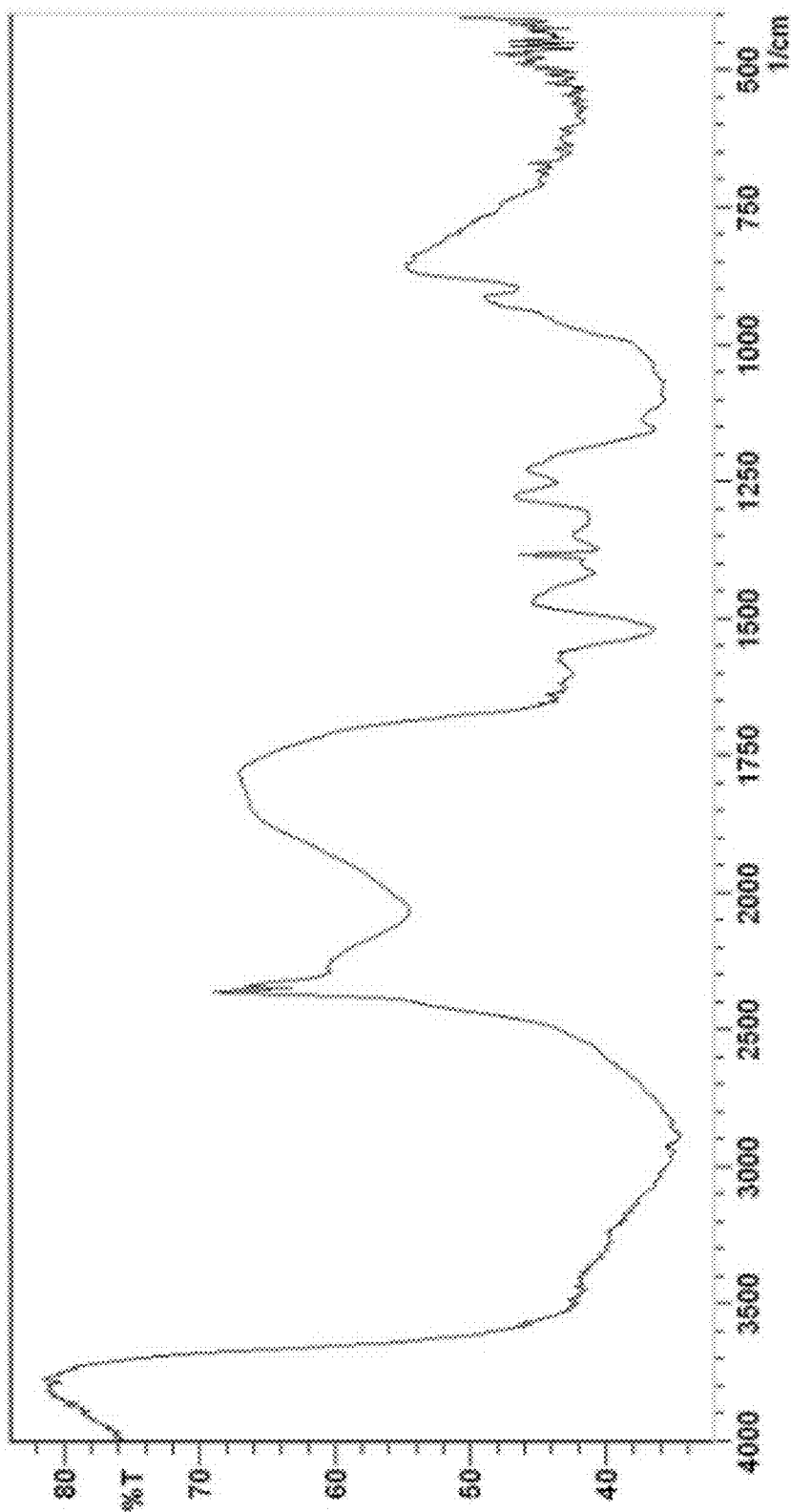
Figure 8A:
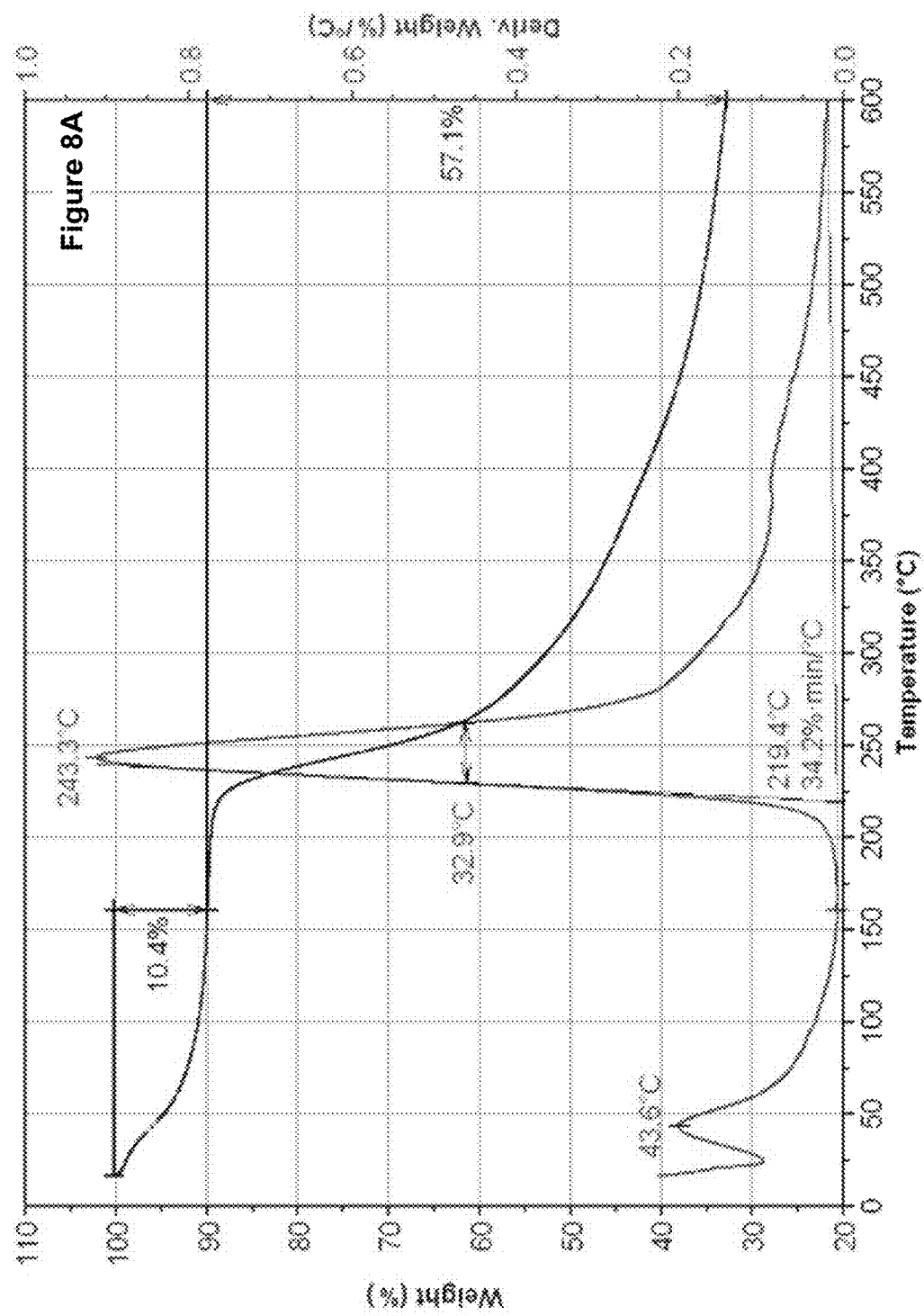
Figure 9A:
FIGS. 9A and 9B show exemplified SEM micrographs respectively for input chitosan (9A) and water-soluble high molecular-weight chitosan (9B).
Figure 9B:

The water-soluble high molecular-weight chitosan produced by the above described methods have been analyzed using several techniques. FIG. 5 shows a solid state 13C-NMR spectrum of the modified water-soluble high molecular-weight chitosan. FIGS. 6A and 6B show powder X-ray diffraction intensity distributions respectively for input chitosan (6A) and water-soluble high molecular-weight chitosan (6B). FIGS. 7A and 7B show exemplified FTIR spectra respectively for input chitosan (7A) and water-soluble high molecular-weight chitosan (7B). FIGS. 8A and 8B show exemplified thermal analysis thermograms respectively for input chitosan (8A) and water-soluble high molecular-weight chitosan (8B). FIGS. 9A and 9B show exemplified SEM micrographs respectively for input chitosan (9A) and water-soluble high molecular-weight chitosan (9B).

What is claimed is:

1. A method for the preparation of high molecular-weight chitosan, which comprises:
   introducing a mixture of input chitosan, alkyl alcohol, water, and an acid into a supercritical fluid vessel;
   heating the mixture in the supercritical fluid vessel to an elevated temperature;
   incubating the mixture at a supercritical pressure for a period of incubation time in the supercritical fluid vessel;
   depressurizing the mixture in the supercritical fluid vessel;
   cooling the mixture in the supercritical fluid vessel to room temperature; and
   collecting a powder comprising water-soluble high molecular-weight chitosan from the supercritical vessel; and wherein the input chitosan is not a water-soluble high molecular-weight chitosan.

2. The method according to claim 1, wherein the input chitosan has a molecular weight in the range 100 kDa to 600 kDa.

3. The method according to claim 1, wherein the input chitosan has a degree of aceylation higher than 50%.

4. The method according to claim 1, wherein the alkyl alcohol has a carbon number in a range $C_3$ to $C_4$ in the chain hydrocarbon chain.

5. The method according to claim 1, wherein the alkyl alcohol is ethanol.

6. The method according to claim 1, wherein the mixture comprises from 5% to 95% of alkyl alcohol based on volume.

7. The method according to claim 1, wherein the acid comprises an organic acid or an inorganic acid.

8. The method according to claim 7, wherein the inorganic acid is hydrochloric acid.

9. The method according to claim 8, wherein the mixture comprises from 10% to 50% of the hydrochloric acid based on the volume of the mixture.

10. The method according to claim 1, wherein the mixture comprises from 10% to 90% of water based on volume.

11. The method according to claim 1, wherein the elevated temperature in the step of heating is in the range 40° C. to 100° C.

12. The method according to claim 1, wherein the pressure in the step of incubating is in the range 40 bar to 100 bar.

13. The method according to claim 1, wherein the step of incubating has an incubation time in is in the range 1 to 3 hours.

14. The method according to claim 1, wherein the mixture comprises NaCl, $CaCl_2$, or an organic co-solvent.

15. The method according to claim 1, wherein the water-soluble high molecular-weight chitosan has an average molecular weight in the range from 500 kDa to 10000 kDa, wherein the water-soluble high molecular-weight chitosan has a viscosity from 500 cps to 5000 cps.

16. The method according to claim 1, wherein the water-soluble high molecular-weight chitosan has water solubility more than 1% in weight/volume concentration.

17. The method according to claim 1, further comprising:
    dissolving the water-soluble high molecular-weight chitosan in water to form a polymer solution; and
    forming a film using the polymer solution comprising the water-soluble high molecular-weight chitosan.

18. The method according to claim 1, further comprising:
    dissolving the water-soluble high molecular-weight chitosan in water to form a polymer solution; and
    coating a food item using the polymer solution.

19. The method according to claim 1, further comprising:
    dissolving the water-soluble high molecular-weight chitosan in water to form a polymer solution; and
    coating a substrate item using the polymer solution to provide anti-bacterial function.

20. The method according to claim 19, wherein the step of coating comprises:
    atomizing the polymer solution to form an atomized polymer solution; and
    spraying the atomized polymer solution on the food item.

* * * * *